(12) United States Patent
Warren et al.

(10) Patent No.: US 8,670,826 B2
(45) Date of Patent: Mar. 11, 2014

(54) METHODS AND DEVICES FOR ADAPTING CHARGE INITIATION FOR AN IMPLANTABLE DEFIBRILLATOR

(75) Inventors: Jay A. Warren, San Juan Capistrano, CA (US); Gust H. Bardy, Carnation, WA (US)

(73) Assignee: Cameron Health, Inc., San Clemente, CA (US)

( * ) Notice: Subject to any disclaimer, the term of this patent is extended or adjusted under 35 U.S.C. 154(b) by 0 days.

(21) Appl. No.: 13/599,513

(22) Filed: Aug. 30, 2012

(65) Prior Publication Data

US 2012/0323290 A1  Dec. 20, 2012

Related U.S. Application Data

(63) Continuation of application No. 13/588,808, filed on Aug. 17, 2012, which is a continuation of application No. 12/359,072, filed on Jan. 23, 2009, now Pat. No. 8,249,702, which is a continuation of application No. 11/042,911, filed on Jan. 25, 2005, now Pat. No. 8,160,697.

(51) Int. Cl.
*A61N 1/368* (2006.01)
*A61N 1/362* (2006.01)

(52) U.S. Cl.
CPC .................... *A61N 1/3621* (2013.01)
USPC ........................................... 607/5

(58) Field of Classification Search
CPC ... A61N 1/361; A61N 1/3622; A61N 1/3624; A61N 1/3712; A61N 1/39; A61N 1/395; A61N 1/3956; A61N 1/3962
USPC .................................................. 607/5, 14, 28
See application file for complete search history.

(56) References Cited

U.S. PATENT DOCUMENTS

| RE30,387 E | 8/1980 | Denniston, III et al. |
| 4,880,005 A * | 11/1989 | Pless et al. ............ 607/15 |
| 4,940,054 A | 7/1990 | Grevis et al. |
| 5,117,824 A | 6/1992 | Keimel et al. |
| 5,129,392 A | 7/1992 | Bardy et al. |

(Continued)

FOREIGN PATENT DOCUMENTS

| AU | 2005325670 B2 | 8/2012 |
| CA | 2766866 A1 | 1/2011 |

(Continued)

OTHER PUBLICATIONS

"U.S. Appl. No. 10/755,185, Final Office Action mailed Sep. 25, 2008", 12 pgs.

(Continued)

*Primary Examiner* — Christopher D Koharski
*Assistant Examiner* — Frances Oropeza
(74) *Attorney, Agent, or Firm* — Schwegman Lundberg & Woessner, P.A.

(57) ABSTRACT

Adaptive methods for initiating charging of the high power capacitors of an implantable medical device for therapy delivery after the patient experiences a non-sustained arrhythmia, and devices that perform such methods. The adaptive methods and devices adjust persistence criteria used to analyze an arrhythmia prior to initiating a charging sequence to deliver therapy. Some embodiments apply a specific sequence of X-out-of-Y criteria, persistence criteria, and last event criteria before starting charging for therapy delivery.

23 Claims, 7 Drawing Sheets

(56) References Cited

U.S. PATENT DOCUMENTS

| | | | |
|---|---|---|---|
| 5,193,535 A | 3/1993 | Bardy et al. | |
| 5,215,098 A | 6/1993 | Steinhaus et al. | |
| 5,217,021 A | 6/1993 | Steinhaus et al. | |
| 5,261,400 A | 11/1993 | Bardy | |
| 5,313,953 A | 5/1994 | Yomtov et al. | |
| 5,331,966 A | 7/1994 | Bennett et al. | |
| 5,342,402 A | 8/1994 | Olson et al. | |
| 5,354,316 A * | 10/1994 | Keimel | 607/15 |
| 5,405,363 A | 4/1995 | Kroll et al. | |
| 5,411,031 A | 5/1995 | Yomtov | |
| 5,413,591 A | 5/1995 | Knoll | |
| 5,531,766 A | 7/1996 | Kroll et al. | |
| 5,620,477 A | 4/1997 | Pless et al. | |
| 5,658,319 A | 8/1997 | Kroll | |
| 5,697,953 A | 12/1997 | Kroll et al. | |
| 5,817,134 A | 10/1998 | Greenhut et al. | |
| 5,827,326 A | 10/1998 | Kroll et al. | |
| 5,836,975 A * | 11/1998 | DeGroot | 607/5 |
| 5,904,705 A | 5/1999 | Kroll et al. | |
| H1905 H | 10/2000 | Hill | |
| 6,169,923 B1 | 1/2001 | Kroll | |
| 6,223,078 B1 | 4/2001 | Marcovecchio | |
| 6,236,882 B1 | 5/2001 | Lee et al. | |
| 6,266,554 B1 | 7/2001 | Hsu et al. | |
| 6,308,095 B1 | 10/2001 | Hsu et al. | |
| 6,334,071 B1 | 12/2001 | Lu | |
| 6,411,844 B1 | 6/2002 | Kroll et al. | |
| 6,438,410 B2 | 8/2002 | Hsu et al. | |
| 6,445,949 B1 | 9/2002 | Kroll | |
| 6,449,503 B1 | 9/2002 | Hsu | |
| 6,574,505 B1 | 6/2003 | Warren | |
| 6,587,720 B2 | 7/2003 | Hsu et al. | |
| 6,587,723 B1 | 7/2003 | Sloman et al. | |
| 6,879,856 B2 * | 4/2005 | Stadler et al. | 607/14 |
| 7,027,856 B2 | 4/2006 | Zhou et al. | |
| 7,103,404 B2 | 9/2006 | Stadler et al. | |
| 7,447,544 B1 | 11/2008 | Kroll | |
| 8,160,697 B2 | 4/2012 | Warren et al. | |
| 8,229,563 B2 | 7/2012 | Warren et al. | |
| 8,249,702 B2 | 8/2012 | Warren et al. | |
| 2001/0027330 A1 | 10/2001 | Sullivan et al. | |
| 2002/0188215 A1 | 12/2002 | Ferek-Petric | |
| 2003/0144700 A1 | 7/2003 | Brown et al. | |
| 2004/0015197 A1 | 1/2004 | Gunderson | |
| 2004/0093035 A1 | 5/2004 | Schwartz et al. | |
| 2004/0171959 A1 | 9/2004 | Stadler et al. | |
| 2004/0215240 A1 | 10/2004 | Lovett et al. | |
| 2004/0230229 A1 | 11/2004 | Lovett et al. | |
| 2004/0254611 A1 | 12/2004 | Palreddy et al. | |
| 2004/0254613 A1 | 12/2004 | Ostroff et al. | |
| 2005/0004615 A1 | 1/2005 | Sanders | |
| 2005/0049644 A1 | 3/2005 | Warren et al. | |
| 2005/0154421 A1 | 7/2005 | Ousdigian et al. | |
| 2006/0036288 A1 | 2/2006 | Bocek et al. | |
| 2006/0079796 A1 | 4/2006 | Marcovecchio et al. | |
| 2012/0316612 A1 | 12/2012 | Warren et al. | |

FOREIGN PATENT DOCUMENTS

| | | |
|---|---|---|
| DE | 29801807 U1 | 6/1998 |
| EP | 0095727 A1 | 12/1983 |
| EP | 0316616 A2 | 5/1989 |
| EP | 0316616 A3 | 5/1989 |
| EP | 0347353 A1 | 12/1989 |
| EP | 0517494 B1 | 12/1992 |
| EP | 0518599 A2 | 12/1992 |
| EP | 0518599 B1 | 12/1992 |
| EP | 0536873 B1 | 12/1992 |
| EP | 0517494 A3 | 3/1993 |
| EP | 0554208 A2 | 8/1993 |
| EP | 0554208 A3 | 1/1994 |
| EP | 0586858 B1 | 3/1994 |
| EP | 0627237 A1 | 12/1994 |
| EP | 0641573 A2 | 3/1995 |
| EP | 0641573 A3 | 3/1995 |
| EP | 0677301 A1 | 10/1995 |
| EP | 0917887 A1 | 5/1999 |
| EP | 0923130 A1 | 6/1999 |
| EP | 1000634 A1 | 5/2000 |
| EP | 1046409 A2 | 10/2000 |
| EP | 1046409 B1 | 10/2000 |
| JP | 2008528103 A | 7/2008 |
| WO | WO-8901802 A1 | 3/1989 |
| WO | WO-9319809 A1 | 10/1993 |
| WO | WO-9729802 A2 | 8/1997 |
| WO | WO-9825349 A1 | 6/1998 |
| WO | WO-9903534 A1 | 1/1999 |
| WO | WO-9937362 A1 | 7/1999 |
| WO | WO-9953991 A1 | 10/1999 |
| WO | WO-0041766 A1 | 7/2000 |
| WO | WO-0050120 A1 | 8/2000 |
| WO | WO-0143649 A1 | 6/2001 |
| WO | WO-0156166 A2 | 8/2001 |
| WO | WO-02068046 A1 | 9/2002 |
| WO | WO-03018121 A2 | 3/2003 |
| WO | WO-2004093974 A2 | 4/2004 |
| WO | WO-2004091720 A2 | 10/2004 |
| WO | WO-2004093974 A3 | 12/2004 |
| WO | WO-2006081027 A2 | 8/2006 |

OTHER PUBLICATIONS

"U.S. Appl. No. 11/042,911, Advisory Action mailed May 15, 2008", 3 pgs.

"U.S. Appl. No. 11/042,911, Advisory Action mailed Nov. 1, 2010", 3 pgs.

"U.S. Appl. No. 11/042,911, Appeal Brief filed Jan. 24, 2011", 29 pgs.

"U.S. Appl. No. 11/042,911, Applicant's Summary of Examiner Interview filed Jul. 10, 2008", 1 pg.

"U.S. Appl. No. 11/042,911, Examiner Interview Summary mailed Apr. 22, 2008", 4 pgs.

"U.S. Appl. No. 11/042,911, Examiner Interview Summary mailed Jun. 12, 2008", 2 pgs.

"U.S. Appl. No. 11/042,911, Final Office Action mailed Feb. 26, 2008", 10 pgs.

"U.S. Appl. No. 11/042,911, Final Office Action mailed Aug. 23, 2010", 8 pgs.

"U.S. Appl. No. 11/042,911, Final Office Action mailed Sep. 16, 2008", 21 pgs.

"U.S. Appl. No. 11/042,911, Final Office Action mailed Oct. 7, 2011", 13 pgs.

"U.S. Appl. No. 11/042,911, Final Office Action mailed Dec. 10, 2009", 14 pgs.

"U.S. Appl. No. 11/042,911, Non Final Office Action mailed Mar. 3, 2010", 7 pgs.

"U.S. Appl. No. 11/042,911, Non Final Office Action mailed Apr. 14, 2011", 13 pgs.

"U.S. Appl. No. 11/042,911, Non Final Office Action mailed Jul. 27, 2007", 10 pgs.

"U.S. Appl. No. 11/042,911, Notice of Allowance mailed Dec. 20, 2011", 8 pgs.

"U.S. Appl. No. 11/042,911, Notice of Non-Compliant Amendment mailed Jul. 17, 2009", 2 pgs.

"U.S. Appl. No. 11/042,911, Response filed Jan. 16, 2009 to Restriction Requirement mailed Dec. 16, 2008", 12 pgs.

"U.S. Appl. No. 11/042,911, Response filed Feb. 10, 2010 to Final Office Action mailed Dec. 10, 2009", 17 pgs.

"U.S. Appl. No. 11/042,911, Response filed Apr. 25, 2008 to Final Office Action mailed Feb. 26, 2008", 20 pgs.

"U.S. Appl. No. 11/042,911, Response filed Apr. 30, 2009 to Restriction Requirement mailed Apr. 2, 2009", 10 pgs.

"U.S. Appl. No. 11/042,911, Response filed Jun. 3, 2010 to Non Final Office Action mailed Mar. 3, 2010", 12 pgs.

"U.S. Appl. No. 11/042,911, Response filed Jul. 14, 2011 to Non Final Office Action mailed Apr. 14, 2011", 7 pgs.

"U.S. Appl. No. 11/042,911, Response filed Aug. 14, 2009 to Notice of Non-Compliant Amendment mailed Jul. 17, 2009", 8 pgs.

(56) References Cited

OTHER PUBLICATIONS

"U.S. Appl. No. 11/042,911, Response filed Oct. 19, 2010 to Final Office Action mailed Aug. 23, 2010", 7 pgs.
"U.S. Appl. No. 11/042,911, Response filed Oct. 22, 2007 to Non Final Office Action mailed Jul. 27, 2007", 17 pgs.
"U.S. Appl. No. 11/042,911, Response filed Nov. 17, 2008 to Final Office Action mailed Sep. 16, 2008", 17 pgs.
"U.S. Appl. No. 11/042,911, Response filed Dec. 7, 2011 to Final Office Action mailed Oct. 7, 2011", 10 pgs.
"U.S. Appl. No. 11/042,911, Restriction Requirement mailed Apr. 2, 2009", 11 pgs.
"U.S. Appl. No. 11/042,911, Restriction Requirement mailed Dec. 16, 2008", 6 pgs.
"U.S. Appl. No. 11/043,012, Advisory Action mailed Nov. 1, 2010", 3 pgs.
"U.S. Appl. No. 11/043,012, Appeal Brief filed Feb. 18, 2011", 21 pgs.
"U.S. Appl. No. 11/043,012, Applicant's Summary of Examiner Interview filed Jul. 10, 2008", 1 pg.
"U.S. Appl. No. 11/043,012, Examiner Interview Summary mailed Apr. 22, 2008", 4 pgs.
"U.S. Appl. No. 11/043,012, Examiner Interview Summary mailed Jun. 13, 2008", 2 pgs.
"U.S. Appl. No. 11/043,012, Final Office Action mailed Feb. 26, 2008", 10 pgs.
"U.S. Appl. No. 11/043,012, Final Office Action mailed Aug. 19, 2010", 13 pgs.
"U.S. Appl. No. 11/043,012, Final Office Action mailed Sep. 25, 2008", 23 pgs.
"U.S. Appl. No. 11/043,012, Final Office Action mailed Dec. 9, 2009", 12 pgs.
"U.S. Appl. No. 11/043,012, Non Final Office Action mailed Mar. 3, 2010", 7 pgs.
"U.S. Appl. No. 11/043,012, Non Final Office Action mailed May 12, 2011", 11 pgs.
"U.S. Appl. No. 11/043,012, Non Final Office Action mailed Jul. 26, 2007", 10 pgs.
"U.S. Appl. No. 11/043,012, Non Final Office Action mailed Dec. 9, 2011", 15 pgs.
"U.S. Appl. No. 11/043,012, Notice of Allowance Mar. 26, 2012", 6 pgs.
"U.S. Appl. No. 11/043,012, Notice of Non Compliant Amendment mailed Jul. 17, 2009", 2 pgs.
"U.S. Appl. No. 11/043,012, Response filed Jan. 16, 2009 to Restriction Requirement mailed Dec. 16, 2008", 13 pgs.
"U.S. Appl. No. 11/043,012, Response filed Jan. 27, 2012 to Non Final Office Action mailed Dec. 9, 2011", 8 pgs.
"U.S. Appl. No. 11/043,012, Response filed Feb. 9, 2010 to Final Office Action mailed Dec. 9, 2009", 18 pgs.
"U.S. Appl. No. 11/043,012, Response filed Apr. 25, 2008 to Final Office Action mailed Feb. 26, 2008", 22 pgs.
"U.S. Appl. No. 11/043,012, Response filed Apr. 30, 2009 to Restriction Requirement mailed Apr. 2, 2009", 11 pgs.
"U.S. Appl. No. 11/043,012, Response filed Jun. 3, 2010 to Non Final Office Action mailed Mar. 3, 2010", 4 pgs.
"U.S. Appl. No. 11/043,012, Response filed Aug. 11, 2011 to Non Final Office Action mailed May 12, 2011", 7 pgs.
"U.S. Appl. No. 11/043,012, Response filed Aug. 14, 2009 to Notice of Non Compliant Amendment mailed Jul. 17, 2009", 9 pgs.
"U.S. Appl. No. 11/043,012, Response filed Oct. 19, 2010 to Final Office Action mailed Aug. 19, 2010", 7 pgs.
"U.S. Appl. No. 11/043,012, Response filed Oct. 26, 2007 to Non Final Office Action mailed Jul. 26, 2007", 18 pgs.
"U.S. Appl. No. 11/043,012, Response filed Nov. 25, 2008 to Final Office Action mailed Sep. 25, 2008", 18 pgs.
"U.S. Appl. No. 11/043,012, Restriction Requirement mailed Apr. 2, 2009", 12 pgs.
"U.S. Appl. No. 11/043,012, Restriction Requirement mailed Dec. 16, 2008", 9 pgs.
"U.S. Appl. No. 12/359,072, Notice of Allowance mailed Mar. 26, 2012", 11 pgs.
"U.S. Appl. No. 12/359,072, Preliminary Amendment filed Dec. 15, 2009", 9 pgs.
"U.S. Appl. No. 12/359,072, Response filed Jan. 19, 2012 to Restriction Requirement mailed Dec. 21, 2011", 10 pgs.
"U.S. Appl. No. 12/359,072, Restriction Requirement mailed Dec. 21, 2011", 6 pgs.
"Australian Application Serial No. 2005325670, Office Action mailed Nov. 12, 2010", 6 pgs.
"Australian Application Serial No. 2012211492, First Examiner Report mailed Dec. 24, 2012", 7 pgs.
"Australian Application Serial No. 2012211492, Response filed Apr. 29, 2013 to First Examiner Report mailed Dec. 24, 2012", 76 pgs.
"Australian Application Serial No. 2012211492, Subsequent Examiners Report mailed Jul. 1, 2013", 4 pgs.
"Canadian Application Serial No. 2,587,938, Office Action mailed Jan. 15, 2013", 5 pgs.
"Canadian Application Serial No. 2,587,938, Office Action mailed Nov. 22, 2013", 4 pgs.
"Canadian Application Serial No. 2,587,938, Response filed Jul. 12, 2013 to Office Action mailed Jan. 15, 2013", 17 pgs.
"Chinese Application Serial No. 200580047119.3, Office Action mailed Jul. 7, 2011", English only, 5 pgs.
"Chinese Application Serial No. 200580047119.3, Office Action mailed Dec. 3, 2010", w/English translation, 27 pgs.
"Chinese Application Serial No. 200580047119.3, Response filed Apr. 18, 2011 to Office Action mailed Dec. 3, 2010", w/English translation, 13 pgs.
"Chinese Application Serial No. 201010173002.2, Response filed Apr. 18, 2011 to Office Action mailed Dec. 3, 2010", 9 pgs.
"European Application Serial No. 05855365.2, Office Action mailed May 8, 2009", 3 pgs.
"European Application Serial No. 05855365.2, Office Action mailed Aug. 26, 2011", 4 pgs.
"European Application Serial No. 05855365.2, Response filed Sep. 15, 2009 to Office Action mailed May 8, 2009", 7 pgs.
"European Application Serial No. 05855365.2, Response filed Dec. 12, 2011 to Office Action mailed Aug. 26, 2011", 9 pgs.
"International Application Serial No. PCT/US2005/046794, International Preliminary Report on Patentability mailed Jul. 31, 2007", 8 pgs.
"International Application Serial No. PCT/US2005/046794, International Search Report mailed Aug. 30, 2006", 4 pgs.
"International Application Serial No. PCT/US2005/046794, Written Opinion mailed Aug. 30, 2006", 7 pgs.
"Japanese Application Serial No. 2007-552143, Office Action mailed Jul. 19, 2011", 3 pgs.
Anderson, Mark H, et al., "Performance of Basic Ventricular Tachycardia Detection Algorithms in Implantable Cardioverter Defibrillators: Implications for Device Programming", Pace, vol. 20 Part I, (Dec. 20, 1997), 2975-2983.
Betts, Tim R, et al., "Inappropriate Shock Therapy in a Heart Failure Defibrillator", Pace, vol. 24, No. 2, (Feb. 2001), 238-240.
Boriani, Guiseppe, et al., "Cardioverter-Defibrillator Oversensing Due to Double Counting of Ventricular Tachycardia Electrograms", International Journal of Cardiology, 66, (1998), 91-95.
Callans, David J, et al., "Unique Sensing Errors in Third-Generation Implantable Cardioverter-Defibrillators", JACC, vol. 22, No. 4, (Oct. 4, 1993), 1135-1140.
Gunderson, et al., "An Algorithm to Predict Implantable Cardioverter-Defibrillator Lead Failure", JACC, vol. 44, No. 9,, (Nov. 2004), 1898-1902.
Jaïs, Pierre, "Pacemaker Syndrome Induced by the Mode Switching Algorithm of a DDDR Pacemaker", PACE, vol. 22, Part I, (1999), 682-685.
Jones, Gregory K, et al., "Considerations for Ventricular Fibrillation Detection by Implantable Cardioverter Defibrillators", American Heart Journal, vol. 127, No. 4, Part 2, (Apr. 1994), 1107-1110.
Kelly, Patricia A, et al., "Oversensing During Ventricular Pacing in Patients with a Third-Generation Implantable Cardioverter-Defibrillator", JACC, vol. 23, No. 7, (Jun. 1994), 1531-1534.

(56) References Cited

OTHER PUBLICATIONS

Leung, Sum-Kin, et al., "Apparent Extension of the Atrioventricular Interval Due to Sensor-Based Algorithm Against Supraventricular Tachyarrhythmias", PACE, vol. 17, Part I, (Mar. 1994), 321-330.

Li, Huagui, et al., "The Mean Ventricular Fibrillation Cycle Length: A Potentially Useful Parameter for Progranuning Implantable Cardioverter Defibrillators", PACE, vol. 21, (Sep. 1998), 1789-1794.

Mirowski, M, et al., "Automatic Detection and Defibrillation of Lethal Arrhythmias-A New Concept", JAMA, vol. 213, No. 4, (Jul. 27, 1970), 615-616.

Nair, Mohan, et al., "Automatic Arrhythmia Identification Using Analysis of the Atrioventricular Association", Circulation, 95(4), (Feb. 1997), 967-973.

Newman, David, et al., "Use of Telemetry Functions in the Assessment of Implanted Antitachycardia Device Efficacy", The American Journal of Cardiology, vol. 70, (Sep. 1, 1992), 616-621.

Olson, Walter H, et al., "Onset and Stability for Ventricular Tachyarrhythmia Detection in an Implantable Pacer-Cardioverter-Defibrillator", IEEE, (1987), 167-170.

Schaumann, Anselm, et al., "Enhanced Detection Criteria in Implantable Cardioverter-Defibrillators to Avoid Inappropriate Therapy", The American Journal of Cardiology, vol. 78 (5A), (Sep. 12, 1996), 42-50.

Schreieck, Jurgen, et al., "Inappropriate Shock Delivery Due to Ventricular Double Detection with a Biventricular Pacing Implantable Cardioverter Defibrillator", PACE, vol. 24, No. 7, (Jul. 2001), 1154-1157.

Theuns, D, et al., "Initial Clinical Experience with a New Arrhythmia Detection Algorithm in Dual Chamber Implantable Cardioverter Defibrillators", Europace, vol. 3, (Jul. 2001), 181-186.

\* cited by examiner

METHODS AND DEVICES FOR ADAPTING CHARGE INITIATION FOR AN IMPLANTABLE DEFIBRILLATOR

RELATED APPLICATIONS

This application is a continuation of U.S. patent application Ser. No. 13/588,808, filed Aug. 17, 2012, now U.S. published patent application Ser. No. 2012-0316612, which is a continuation of U.S. patent application Ser. No. 12/359,072, filed Jan. 23, 2009 and now U.S. Pat. No. 8,249,702, which is a continuation of U.S. patent application Ser. No. 11/042,911, filed Jan. 25, 2005 and now U.S. Pat. No. 8,160,697, the entire disclosures of which are herein incorporated by reference.

The present application is related to U.S. patent application Ser. No. 11/043,012, filed Jan. 25, 2005 and now U.S. Pat. No. 8,229,563, which is titled DEVICES FOR ADAPTING CHARGE INITIATION FOR AN IMPLANTABLE CARDIOVERTER-DEFIBRILLATOR.

FIELD

The present invention relates generally to implantable cardiac systems that detect, sense and classify cardiac signals. More particularly, the present invention relates to implantable medical devices that can adapt the initiation of a therapeutic therapy for patients who experience recurring non-sustained arrhythmic episodes.

BACKGROUND

Ventricular tachycardia (VT) is a difficult clinical problem for the physician. Its evaluation and treatment are complicated because it often occurs in life-threatening situations that dictate rapid diagnosis and treatment. VT is defined as three or more beats of ventricular origin in succession at a rate greater than 100 beats/minute. The rhythm is frequently regular, but on occasion it may be modestly to wholly irregular. The arrhythmia may be either well-tolerated or associated with grave, life-threatening hemodynamic compromise. The hemodynamic consequences of VT depend largely on the presence or absence or myocardial dysfunction (such as might result from ischemia or infarction) and on the rate of VT.

VT can be referred to as sustained or nonsustained. Sustained VT refers to an episode that lasts at least 30 seconds and generally requires termination by antiarrhythmic drugs, antitachycardia pacing techniques or electrical cardioversion. Nonsustained VT refers to episodes that are longer than three beats but terminate spontaneously generally within 30 seconds.

Implantable cardiac rhythm management devices are an effective treatment in managing irregular cardiac rhythms in particular patients. Implantable cardiac rhythm management devices are capable of recognizing and treating arrhythmias with a variety of therapies. For the reasons stated above, and for other reasons stated below, which will become apparent to those skilled in the art upon reading and understanding the present specification, there is a need in the art for providing a method for adapting the initiation of a therapeutic therapy for those patients who experience recurring non-sustained arrhythmic episodes.

SUMMARY

The present invention, in an illustrative embodiment, includes a method of cardiac treatment using an implanted medical device system having implanted electrodes and an energy storage system for storing electric charge for use in cardiac stimulus, the method comprising determining that cardiac stimulus is indicated at a first time, initiating a charging operation for the energy storage system, determining whether the cardiac stimulus is no longer indicated at a second time after the first time but prior to delivery of the indicated cardiac stimulus, and, if the cardiac stimulus is no longer indicated, changing a threshold used to determine whether cardiac stimulus is indicated. The second time may occur prior to completion of the charging operation, and/or after completion of the charging operation. The determining step may be performed repeatedly during the charging operation. If the cardiac stimulus continues to be indicated during the charging operation, the determining step may be performed at least once after the charging operation is completed. If the determining step fails, the method may further include delivering cardiac stimulus.

Another illustrative embodiment includes a method of cardiac treatment using an implantable medical device system having implanted electrodes and an energy storage system for storing charge for performing cardiac electrical stimulus, the method comprising capturing a predetermined number of selected cardiac events using the implanted electrodes, determining whether a threshold proportion of the predetermined number of selected cardiac events are abnormal, and, if treatment is indicated: initiating a charging operation for the energy storage system, and determining whether cardiac rhythm has returned to normal and, if so, increasing the threshold proportion. The threshold proportion may be, at least initially, in the range of 70-80%. The step of increasing the threshold proportion may include increasing the predetermined number. The illustrative method may further comprise determining if treatment is indicated if: at least the threshold proportion of the predetermined number of selected events are abnormal, and at least the threshold proportion of the predetermined number of selected events is abnormal for at least a threshold number of events out of a preselected number of events. If the threshold proportion is increased, the method may also include increasing the threshold number and the preselected number.

Yet another illustrative embodiment includes a method of cardiac treatment using an implantable medical device system having implanted electrodes and an energy storage system for storing charge for performing cardiac electrical stimulus, the method comprising capturing a predetermined number of selected cardiac events using the implanted electrodes, observing whether a cardiac condition exists for at least one of the selected cardiac events, determining whether the cardiac condition persists for at least a threshold duration or threshold number of cardiac events, and, if so: initiating a charging operation for the energy storage system, and determining whether cardiac condition has terminated prior to delivery of cardiac stimulus and, if so, extending the threshold duration or increasing the threshold number.

Another illustrative embodiment includes a method of operating an implantable electrical device disposed for providing cardiac stimulus to a patient's heart, the method comprising observing electrical activity in a patient's thorax to discern cardiac function, using the discerned cardiac function to establish a metric related to the patient's cardiac function, determining whether treatment is indicated by comparing the metric to a threshold, preparing to deliver treatment by charging an energy storage means coupled to the operational circuitry, observing whether treatment continues to be indicated, and: if treatment continues to be indicated, discharging energy from the energy storage means to the patient, or, if treatment is no longer indicated, changing the threshold. The metric may be related to a proportion of cardiac events that are abnormal within a set of cardiac events, and/or the metric may be related to a duration of time or a number of sensed cardiac events in which a malignant cardiac condition is detected.

Yet another illustrative embodiment includes a method of operation for an implantable medical device having an energy storage system for storing and delivering therapeutic cardiac stimulus, the method comprising observing cardiac function using implanted electrodes by capturing signals from the implanted electrodes and analyzing the captured signals using operational circuitry associated with the implantable medical device, determining whether electrical cardiac stimulus is likely indicated using a first metric; if so, verifying that electrical cardiac stimulus is indicated using a second metric; if so, initiating a charging operation for the energy storage system; after initiating the charging operation, at least once checking that one of the first metric or the second metric continues to indicate electrical cardiac stimulus, and, if not, modifying a threshold used for comparison with either: the first metric in the determining step, and/or the second metric in the verifying step, to cause the threshold to become more rigorous. The checking step may be performed at least once during the charging operation. The checking step may also be performed at least once after the charging operation is completed.

Another illustrative embodiment includes a method of operating an implantable medical device, the method comprising observing a first threshold to determine whether a patient in which the medical device is implanted likely needs cardiac stimulus, and, if so, observing a second threshold to determine whether the cardiac stimulus is currently indicated, and, if so, initiating a charging sequence for an energy storage system configured for stimulus delivery to the patient; if not, returning to the step of observing the first threshold. The method may include, if the charging sequence is initiated, performing the following steps if the charging sequence is completed: observing a third threshold to determine whether cardiac stimulus is currently indicated; and if so, delivering cardiac stimulus to the patient using implanted electrodes; if not, observing the first threshold to determine whether the patient likely needs cardiac stimulus. If the patient still likely needs cardiac stimulus, the method may include returning to the step of observing the third threshold, or if the patient no longer likely needs cardiac stimulus, adjusting at least one of the first threshold and the second threshold. The method may further include observing whether the first threshold remains crossed during a time period between initiation and completion of the charging sequence and: if so, continuing the charging sequence until completion; or, if not, stopping the charging sequence and changing at least one of the first threshold and the second threshold.

Yet another illustrative embodiment includes a method of cardiac treatment using an implanted medical device system having implanted electrodes and an energy storage system for storing electric charge for use in cardiac electrical stimulus, the method comprising A) determining whether an abnormal event threshold is crossed, the abnormal event threshold being crossed if a specified number of abnormal events occur within a selected number of most recent detected cardiac events, and, if so: determining whether the abnormal event threshold has been exceeded for a threshold number of most recent events and observing whether a most recent events is abnormal, and, if so, initiating a charge sequence for the energy storage system. Once the charge sequence is complete, the method may further include B) determining whether a most recent event is abnormal and, if so, delivering therapeutic energy to the patient; and if not, determining whether the abnormal event threshold remains exceeded when measured from a most recent event; and: if so, waiting for a next cardiac event and again performing step B); or if not, raising the threshold number of most recent events and returning to step A). The method may further include determining whether the abnormal event threshold continues to be crossed while the charge sequence is being performed. Another illustrative embodiment includes a method of operating an implanted medical device system having implanted electrodes and an energy storage system for storing electric charge for use in cardiac electrical stimulus, the method comprising observing a cardiac rate for a patient, and if the cardiac rate exceeds a predetermined rate threshold, performing the above method.

Another illustrative embodiment includes a method of operation for an implanted medical device having implanted electrodes, an energy storage system for storing and delivering cardiac stimulus to a patient, and operational circuitry for operating the device, the method comprising capturing a number of cardiac events, determining whether a first cardiac event, along with a set of previously captured cardiac events, indicates a malignant cardiac condition and, if so, flagging the first cardiac event, observing whether a threshold number of cardiac events within a set of cardiac events have been flagged; if so, initiating a charging sequence for charging the energy storage system in preparation for delivery of electrical cardiac stimulus. The illustrative method further includes, after the charging sequence is initiated, at least once observing whether treatment of the patient continues to be indicated due to a malignant cardiac condition; and, if treatment is no longer indicated, modifying the size of the threshold number and/or the set of cardiac events.

Another illustrative embodiment includes a method including implanting an implantable electrical device in the patient, wherein the device is configured to operate as noted in any the above illustrative embodiments.

DETAILED DESCRIPTION

The following detailed description should be read with reference to the drawings, in which like elements in different drawings are numbered identically. The drawings, which are not necessarily to scale, depict selected embodiments and are not intended to limit the scope of the invention. Those skilled in the art will recognize that many of the examples provided have suitable alternatives that may be utilized.

The present invention is generally related to implantable cardiac treatment systems that provide therapy for patients who are experiencing particular arrhythmias including, for example, ventricular tachycardia. The present invention is directed toward therapy delivery architectures for use in cardiac rhythm devices, as well as devices incorporating such architectures. In particular, the present invention is suited for implantable cardiac treatment systems capable of detecting and treating harmful arrhythmias.

Figure 1A:
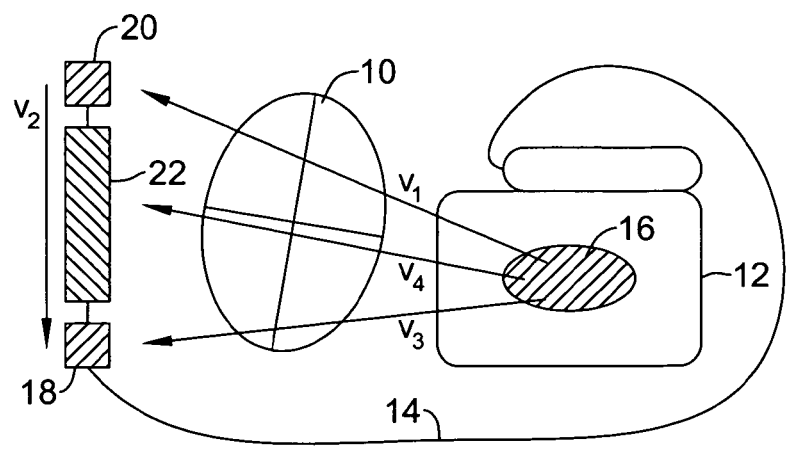
FIGS. 1A-1B illustrate, respectively, representative subcutaneous and transvenous implantable cardiac treatment systems.
Figure 1B:
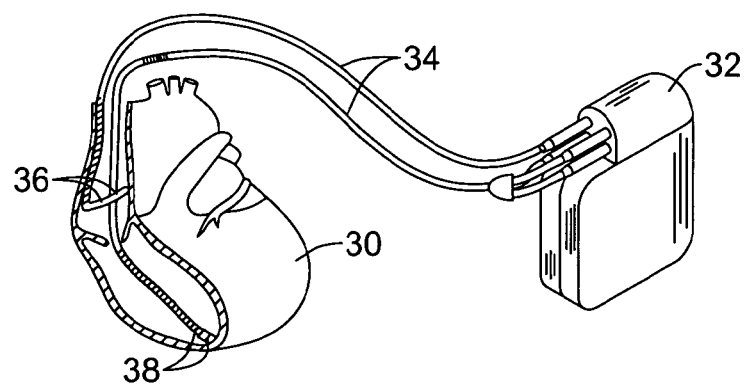

To date, implantable cardiac treatment systems have been either epicardial systems or transvenous systems such as the transvenous system implanted generally as shown in FIG. 1B. However, as further explained herein, the present invention is also adapted to function with a subcutaneous implantable cardiac treatment system as shown in FIG. 1A.

FIG. 1A illustrates a subcutaneously placed implantable cardiac treatment system, in particular, an implantable cardioverter/defibrillator (ICD) system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, in or on the heart muscle, or the patient's vasculature.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

The present invention may be embodied by operational circuitry including select electrical components provided within the canister 2 (FIG. 1A) or canister 11 (FIG. 1B). In such embodiments, the operational circuitry may be configured to enable the methods to be performed. In some similar embodiments, the present invention may be embodied in readable instruction sets such as a program encoded in machine or controller readable media, wherein the readable instruction sets are provided to enable the operational circuitry to perform the analysis discussed in the described embodiments. Further embodiments may include a controller or microcontroller adapted to read and execute the described methods.

The cardiac rhythm management device, whether subcutaneous or transvenous, senses cardiac signals from the patient's heart. The manner in which the data is collected and the type of data collected is dependent on the cardiac rhythm management device being used. Moreover, the cardiac rhythm management device may be programmed to, or may automatically adapt to, optimally detect a particular form of data which is sought by the cardiac rhythm management device.

Figure 2:
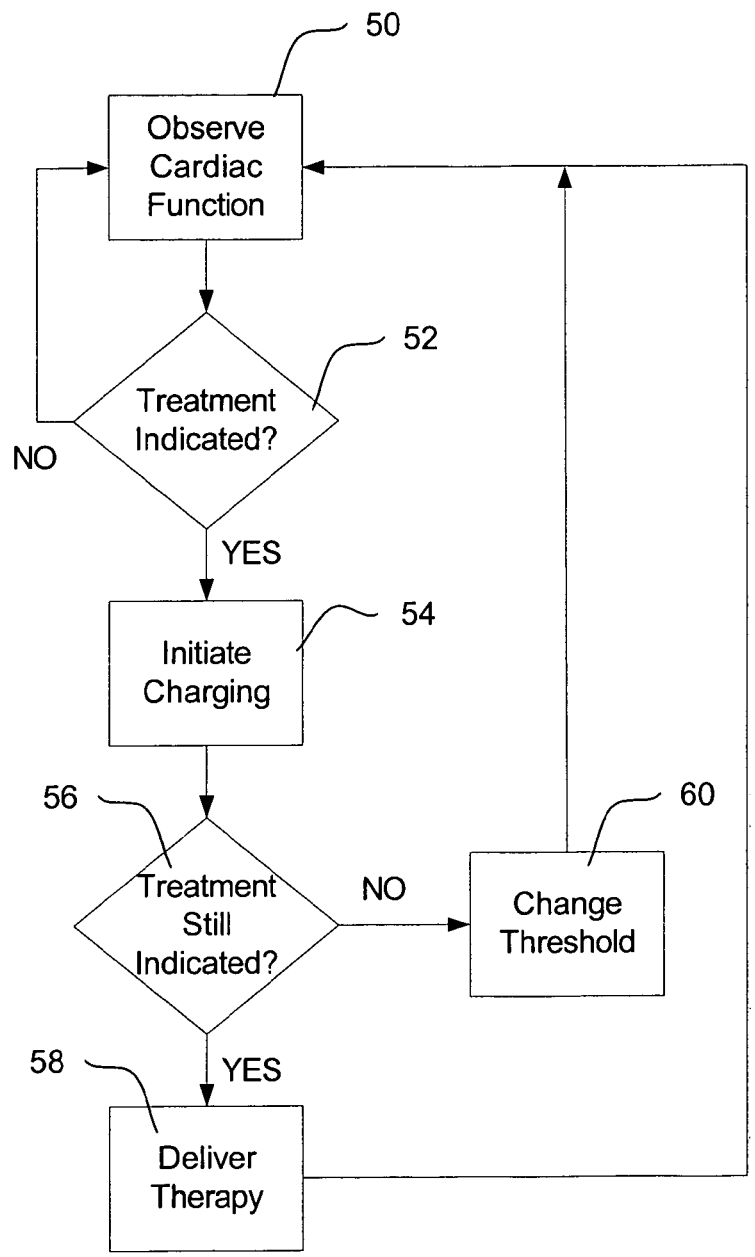
FIG. 2 shows an illustrative method for delivering therapy.

FIG. 2 shows an illustrative method for delivering therapy. As shown, the method includes a first step of observing cardiac function, as shown at 50. The method determines whether treatment is indicated, as shown at 52. Treatment may be indicated by a number of different methods, for example, by reliance upon any number of characteristics or features of the sensed cardiac function. For the illustrative method, treatment may be indicated by the use of a defined threshold. The threshold utilized may take any number of forms depending upon the device's functionality. For example, the threshold may relate to cardiac event rates, cardiac event intervals, lack of cardiac events (asystole or fibrillation), cardiac event morphology (QRS width being an example), or event-to-event correlation.

If treatment is indicated, the method goes on to begin a charging operation, as shown at 54. The initiation of the charge is stored in an associated energy system (sometimes a capacitor or bank of capacitors). During and/or after the charging operation is completed, the method then includes the step of determining whether treatment is still indicated, as shown at 56. If treatment is still indicated when charging is complete (and/or at intermediate times during charging, if so enabled) then the therapy is delivered as shown at 58. If step 56 is performed while charging is occurring, then charging may continue until charging is completed. If treatment is no longer indicated when step 56 is performed, then the method includes changing the threshold, as shown at 60. In an illustrative embodiment, the threshold may be changed to make the threshold more rigorous for satisfying. By making the threshold more rigorous, it is believed that it is less likely that a charge initiation will commence (step 52) without ultimately delivering a therapy (step 58).

Figure 3:
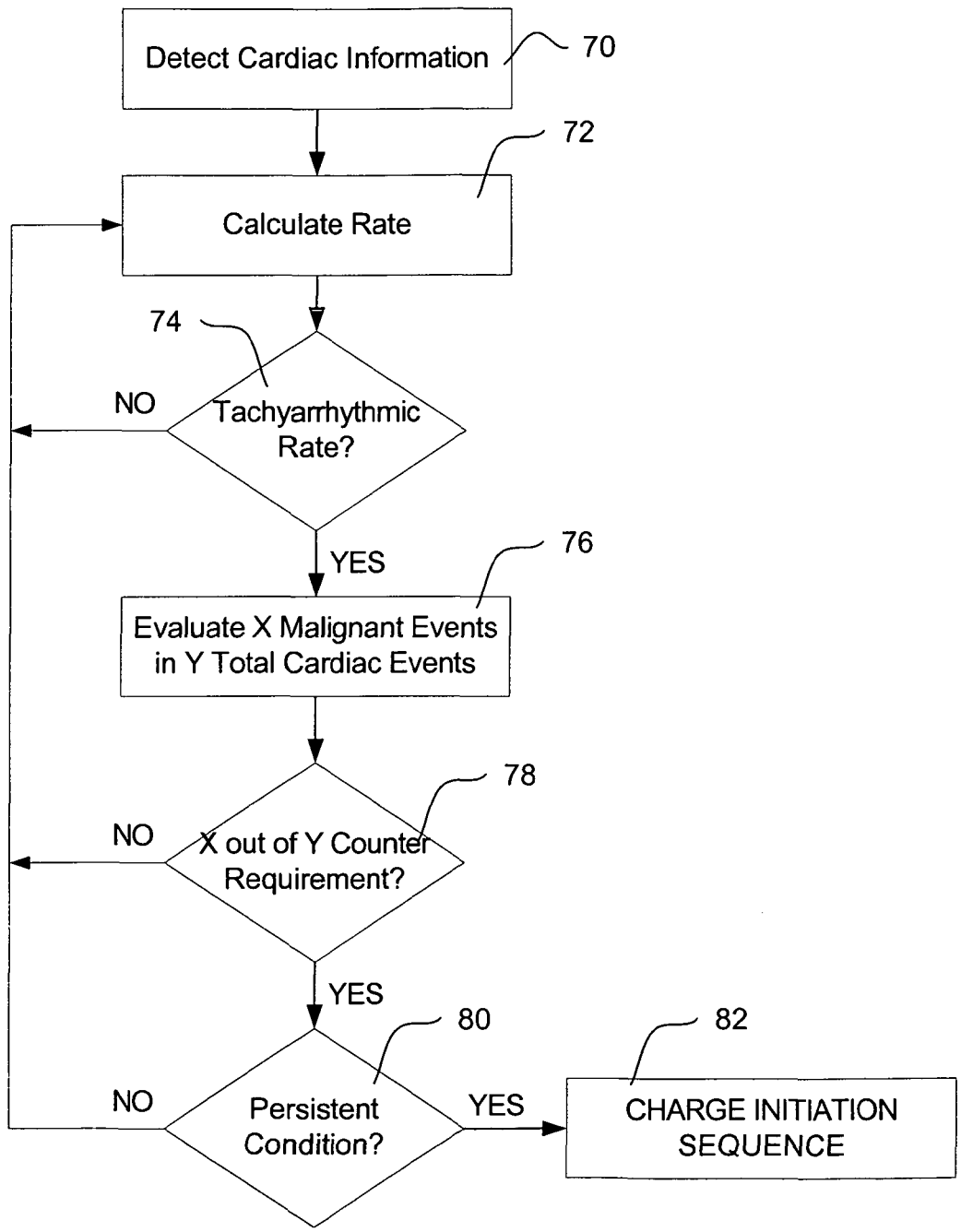
FIG. 3 depicts a charge initiation scheme in accordance with an illustrative embodiment of the present invention.
Figure 4A:
FIGS. 4A-4C depict heart rhythm sections where each individual cardiac event is characterized.
Figure 4B:
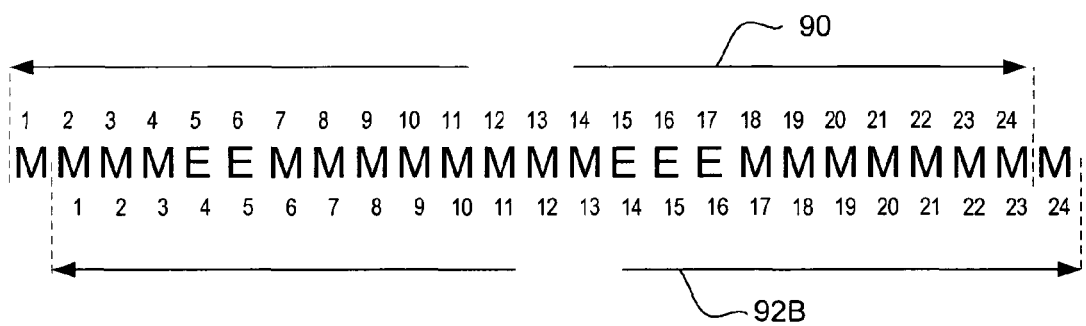
Figure 4C:
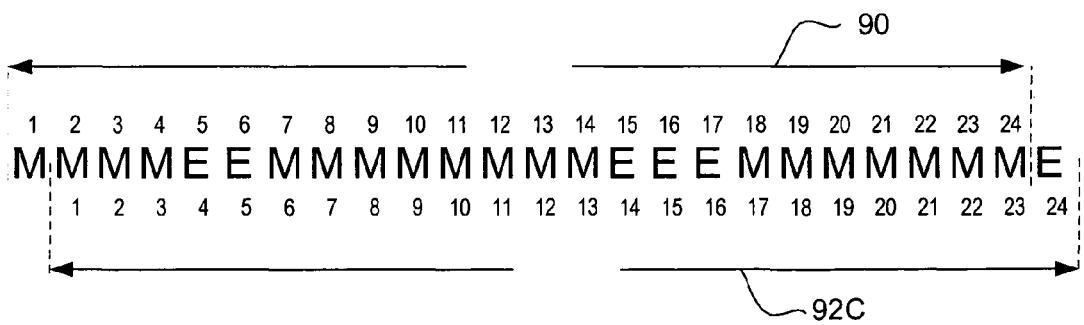
Figure 5:
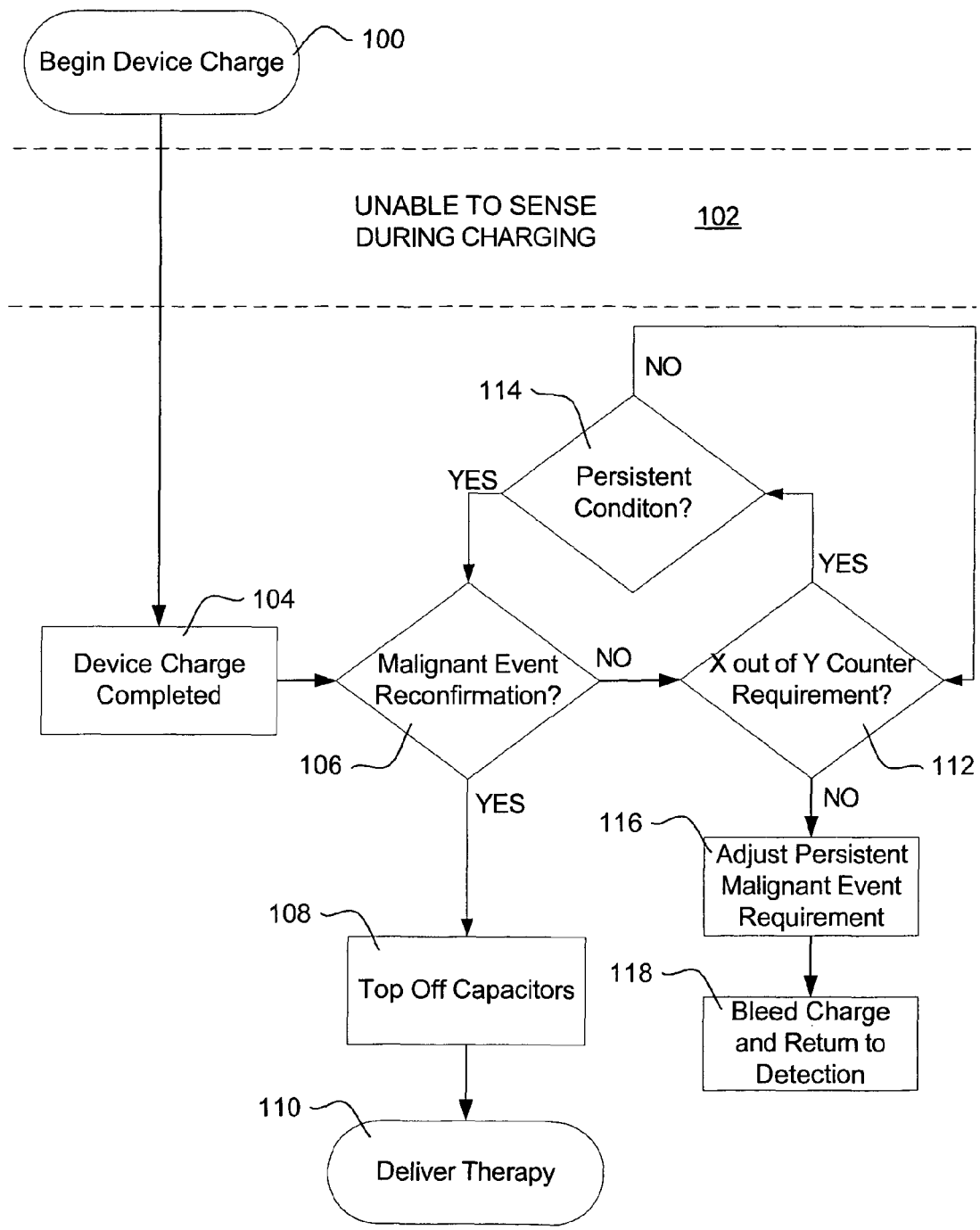
FIG. 5 depicts a charge initiation sequence where an illustrative cardiac rhythm management device is unable to sense during charging.
Figure 6:
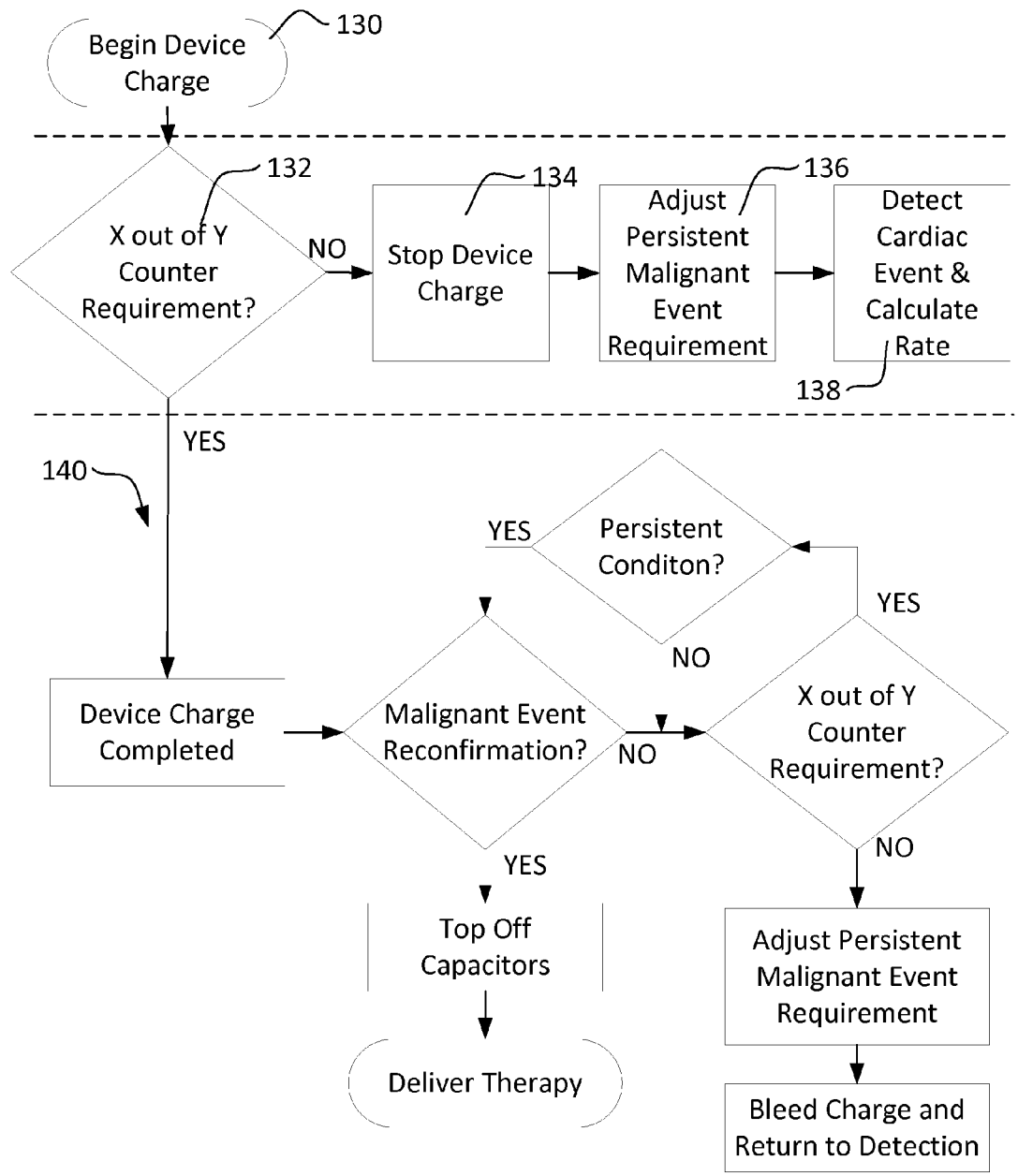
FIG. 6 depicts a charge initiation sequence where an illustrative cardiac rhythm management device is able to sense during charging.

The following illustrative example, encompassing FIGS. 3 and 4A-4C, with further illustration shown in FIGS. 5-6, is a relatively complete example. It should be understood that the claims which follow recite parts of the illustrative methods shown, and that not all steps or aspects of the illustrative example are necessary to the invention. Instead, the relatively complete example shown in FIGS. 3-6 is aiding the understanding of those of skill in the art.

FIG. 3 depicts a charge initiation method in accordance with an illustrative embodiment of the present invention. The illustrative cardiac rhythm management device detects cardiac information, as shown at 70, which includes raw signal data from the patient. This raw signal data may be preprocessed by the device, if so required or desired. Preprocessing steps may include smoothing of the detected data, differentiation, filtering and/or other preprocessing methodologies known in the art.

Detected data, whether preprocessed or raw, is then classified as being either a cardiac event (a heartbeat) or not a cardiac event (extraneous noise). This classification may merely be an initial determination. In particular embodiments, sensed events may then be secondarily examined in an additional waveform appraisal phase. The waveform appraisal phase further appraises the sensed cardiac events and substantiates the classification of those detected signals as true cardiac events. Illustrative details of an example waveform appraisal method are disclosed in detail in U.S. patent application Ser. No. 10/858,598, filed Jun. 1, 2004, now U.S. Pat. No. 7,248,921 and titled METHOD AND DEVICES FOR PERFORMING CARDIAC WAVEFORM APPRAISAL, the disclosure of which is incorporated herein by reference.

Whether from the raw or appraised cardiac data, the illustrative cardiac rhythm management device may then calculate a patient's representative cardiac rate, as shown at 72. In one embodiment, the cardiac rate is calculated from the average R-R interval between four (4) consecutive sensed cardiac events. Other methods known in the art for calculating a patient's cardiac rate may also be utilized.

The illustrative cardiac rhythm management device then assesses whether the cardiac rate is tachyarrhythmic, as shown at 74. Cardiac rates in excess of 100 bpm are defined as tachyarrhythmias in adults. For most patients, however, a higher cardiac rate threshold is more indicative of a pathologic tachyarrhythmia. Some illustrative embodiments of the invention account for this inconsistency with patients by permitting a physician to adjust the cardiac rate threshold to meet the needs of a particular patient. For example, a physician may adjust the cardiac rate threshold to 120 bpm, instead of 100 bpm, to indicate tachyarrhythmia. This attribute is particularly beneficial for children, who generally have higher pathologic tachyarrhythmic thresholds (around 180 bpm) than adults.

When a patient's cardiac rate is below the tachyarrhythmic threshold, the illustrative cardiac rhythm management device takes no further action other than to continue monitoring the patient's cardiac rate. However, in instances where a patient's cardiac rate does exceed the threshold, the illustrative device then further evaluates the individual cardiac events giving rise to the tachyarrhythmic rate. In particular, the illustrative device first employs an X out of Y counter, as shown at 76.

The individual cardiac events giving rise to a tachyarrhythmic rate are hereinafter defined as "malignant cardiac events" and are the X constituent in the counter. The Y constituent for the counter comprises the total number of cardiac events being evaluated (whether malignant or non-malignant). In a preferred embodiment, the cardiac rhythm management device requires eighteen (18) malignant cardiac events out of twenty-four (24) total detected events to prompt the cardiac rhythm management device to initiate a second level of evaluation, as shown by the decision at 78. Alternative X out of Y quotients may also be used with the present invention.

If the X out of Y counter requirement is not met, then the device continues to monitor the patient's cardiac rate until the X out of Y counter requirement is satisfied, if ever. Once the counter requirement is satisfied, the device evaluates the persistence of the malignant cardiac events, as shown at 80.

The persistence condition of the illustrative embodiment is a gate-keeper step. As the gate-keeper, the persistence condition is the last condition that must be satisfied prior to the illustrative device initiates the charging of its capacitors for therapy delivery, as shown at 82. It is believed that the persistence condition will reduce the number of unnecessary device charge initiations. This is particularly true for those patients who suffer from non-sustained ventricular arrhythmias. Reducing inappropriate charges increases the longevity of the device's batteries and ultimately the longevity of the device itself. This subsequently benefits the patient by reducing the frequency of device replacements.

The illustrative persistence condition evaluates a cardiac rhythm's persistence in satisfying the X out of Y counter requirement. Specifically, the persistence condition evaluates two questions relating to the X out of Y counter:
(1) Is the X out of Y counter requirement satisfied sequentially for a defined 'x' number of times?
(2) Does the last cardiac event in the final X out of Y counter requirement indicate a malignant cardiac event?

In an illustrative embodiment, the persistence condition is (at least initially) satisfied when the X out of Y counter requirement is satisfied sequentially for two (2) times. Examples illustrating the persistence condition are depicted in FIGS. 4A-4C.

FIGS. 4A-4C depict heart rhythm sections where each individual cardiac event is characterized. More specifically, the FIGS. depict a sequence 90 of cardiac events where the "M" symbol represents a malignant cardiac event and the "E" symbol represents a non-malignant cardiac event.

In FIG. 4A, nineteen (19) malignant events are shown in twenty-four (24) cardiac events. According to an 18 out of 24 counter requirement, the section of cardiac events depicted satisfies the X out of Y counter requirement. Since the counter requirement is satisfied, the device may then evaluate the persistence condition. In doing so, the device flags this X out of Y counter as the first success for evaluating the persistence condition.

FIG. 4B similarly depicts the sequence 90 of twenty-four (24) cardiac events in FIG. 4A, but additionally includes a newly sensed twenty-fifth (25) cardiac event that is malignant, forming another sequence 92B of twenty-four (24) cardiac events. With the addition of the new cardiac event, the cardiac rhythm management device again evaluates the X out of Y counter requirement. Now, the last sequence 92B of twenty-four (24) cardiac events includes twenty (20) malignant events. Thus, the X out of Y counter requirement is again satisfied and the device flags this successive X out of Y counter. The illustrative device's operational circuitry then evaluates the persistence condition. The first inquiry of the persistence condition is satisfied because two sequential X out of Y counter requirements were met. Additionally, the second inquiry of the persistence condition is satisfied because the last cardiac event in the second and final X out of Y counter requirement was a malignant event. As a result, the illustrative device's operational circuitry then initiates the charging of the device's capacitors for therapy delivery.

FIG. 4C also depicts the sequence 90 of twenty-four (24) cardiac events in FIG. 4A, but instead includes a newly sensed twenty-fifth (25) cardiac event that is normal, or at least non-malignant, forming another sequence 92C of twenty-four (24) cardiac events. When the cardiac rhythm management device again evaluates the X out of Y counter requirement, it observes that the last sequence 92B of twenty-four (24) cardiac events include eighteen (18) malignant events. Thus, the X out of Y counter requirement is again satisfied and the device flags this successive X out of Y counter. The illustrative device's operational circuitry then evaluates the persistence condition. The first inquiry of the persistence condition is satisfied because two sequential X out of Y counter requirements were met. However, the second inquiry of the persistence condition fails. Specifically, the last cardiac event in the second and final X out of Y counter requirement was not a malignant event. Thus, the device refrains from charge initiation.

Once the gate-keeping function of the persistence condition is satisfied, the device begins to charge its capacitors. FIGS. 5 and 6 depict two alternative scenarios for charging. FIG. 5 depicts a charge initiation sequence where an illustrative cardiac rhythm management device is unable to sense during charging. More specifically, once the device initiates its charging cycle, as shown at 100, the device cannot sense, as shown during time period 102. The method resumes once the device charge is completed, as shown at 104. Since the illustrative cardiac rhythm management device cannot sense during charging, the device must wait until the capacitors are fully charged before the operational circuitry may resume sensing. Immediately following charge completion 104, however, the device reconfirms that therapy delivery is necessary as shown at 106.

In one embodiment, the reconfirmation process is deemed successful if two consecutive malignant events occur within six (6) contiguous cardiac events, with the six (6) events being the most recent events available for evaluation. If the conditions set forth in the reconfirmation process 106 are satisfied, then the capacitors are again charged to their fullest (if necessary) as shown at 108, and therapy is delivered to the patient, as shown at 110.

Alternatively, if the reconfirmation process 106 fails, the device again employs an X out of Y counter requirement, as shown at 112, and must again satisfy the persistence condition, as shown at 114. If at any time the persistence condition and the reconfirmation process are satisfied, then the capacitors are again charged to their fullest, as shown at 108, and therapy is delivered to the patient, as shown at 110. However, if the patient converts to a normal sinus rhythm after charging (or otherwise fails the X out of Y counter requirement), then the parameters set for the persistence condition are modified, as shown at 116, and the capacitors are bled of their charge, as shown at 118.

In addition to being a gate-keeper, the persistence condition is also adaptive to the particular needs of a patient. If a patient frequently suffers from non-sustained tachyarrhythmias, the persistence conditions may be adjusted to help eliminate premature charge initiations. In one embodiment, the first inquiry is further defined to account for this adaptability:

(1) Is the X out of Y counter requirement satisfied sequentially for (3*n)+2 times, where n is an integer with limits between 0 and 5, and further wherein n starts at 0 and increases one integer with each aborted charge initiation?

The second inquiry remains the same. With this expanded definition, the persistence condition's first inquiry requires:

two (2) sequential X out of Y counter requirements satisfied if the device has never aborted a charge initiation;

five (5) sequential X out of Y counter requirements satisfied if the device has aborted a charge initiation once;

eight (8) sequential X out of Y counter requirements satisfied if the device has aborted a charge initiation twice;

eleven (11) sequential X out of Y counter requirements satisfied if the device has aborted a charge initiation three times;

fourteen (14) sequential X out of Y counter requirements satisfied if the device has aborted a charge initiation four times; and seventeen (17) sequential X out of Y counter requirements satisfied if the device has aborted a charge initiation five times.

In all other aspects, the illustrative persistence condition operates as described in detail above with reference to FIGS. 3 and 4A-4C.

FIG. 6 illustrates a portion of the charge initiation sequence where the operational circuitry can sense cardiac events while the device is charging. Cardiac events that are sensed during charging are evaluated and assessed similarly to those being sensed when the device is not charging or otherwise preparing to deliver therapy. Therefore, the cardiac rhythm management device may calculate a cardiac rate and evaluate the frequency of malignant events during the charging cycle. As such, after the device initiates its charging, as shown at 130, the device begins monitoring the X out of Y requirement, as shown at 132. If at any time during the device's charge cycle the patient converts to a normal sinus rhythm after charging (or otherwise fails the X out of Y counter requirement), then the device stops charging, as shown at 134. Additionally, the capacitors are bled of their charge and the parameters set for the persistence condition are modified, as shown at 136, by applying the expanded definition for the first inquiry described above. The method then returns to detection and rate calculation, as shown at 138. Alternatively, if the patient remains in a tachyarrhythmic state throughout the charge cycle, then the device reconfirms that therapy delivery is necessary through the reconfirmation process, following a method similar to that shown in FIG. 5, as indicated at 140.

In the above illustrative embodiment shown in FIGS. 3-6, the term "malignant event" was defined as an event indicative of a tachyarrhythmic rate. In other embodiments, any detected cardiac event that, upon analysis, is indicative of a malignant condition (i.e. a cardiac condition requiring intervention) may be considered a malignant event. An example of a malignant event satisfying other criteria may be an event or series of events having a morphology (for example, shape, QRS width, consecutive event correlation waveform analysis, etc.) indicative of a malignant arrhythmia. Some examples of analysis for providing such determinations are shown in U.S. patent application Ser. No. 10/856,084, filed May 27, 2004, now U.S. Pat. No. 7,330,757 and titled METHOD FOR DISCRIMINATING BETWEEN VENTRICULAR AND SUPRAVENTRICULAR ARRHYTHMIAS, the disclosure of which is incorporated herein by reference. In an example in U.S. Pat. No. 7,330,757, analysis may include tiered assessment including identifying an event as indicative of malignant arrhythmia if it indicates a rate that exceeds a high rate boundary or if the event indicates a rate that is between a low rate boundary and the high rate boundary and the event meets detection enhancement criteria which are discussed throughout the '757 patent.

In alternative embodiments, several portions of the method may be modified. For example, the X out of Y count requirement may be changed to use different parameters (instead of 18 out of 24, other ratios may be used). In yet another embodiment, rather than an X out of Y counter requirement, a group of cardiac events may be analyzed to determine a group correlation waveform score. If the correlation is sufficiently low, it may be determined that cardiac function is erratic to a degree indicating a need for therapeutic delivery. In yet another modification, the persistence conditions themselves may also change. For example, the persistence condition may require longer or shorter analytical periods, consideration of morphology, noise considerations, or the like.

In some embodiments, other conditions may be modified after a patient has spontaneously recovered from a non-sustained tachyarrhythmia or other malignant condition. For instance, rather than altering the persistence condition, the X of Y counter requirement may be changed. More specifically, if an illustrative method begins with an 18 out of 24 counter requirement, the X out of Y counter requirement may extend to a larger number, higher percentage, or other requirement. For example, the 18 out of 24 counter requirement may adjust to 20 out of 24 and/or 21 out of 27. This change may be further incremented with each successive non-sustained ventricular tachyarrhythmia. For example, after the first aborted charge, the 18 out of 24 counter requirement becomes 21 out of 27, which becomes 24 out of 30 on the second aborted charge and 27 out of 33 on the third aborted charge. In alternative illustrative embodiments, more than one rule for a given persistence condition may be changed at the same time.

Some embodiments may make use of a pure rate-driven shocking determination which does not make use of the X out of Y counter requirement. For example, if the cardiac rate observed to initiate the method shown in FIG. 3 (the query "tachyarrhythmic rate?") exceeds a predetermined threshold, it may be determined that therapy is appropriate. Then, at a later time (e.g., during charging of the illustrative device's energy storage system or after charging is complete) the rate may be checked again. Re-checking the conditions giving rise to a decision to deliver therapy at a later time may reveal that stimulus is no longer indicated. In response, a system may raise the threshold cardiac rate for shocking, or may extend a relevant time period in which such a threshold cardiac rate must be held to initiate charging.

Figure 7:
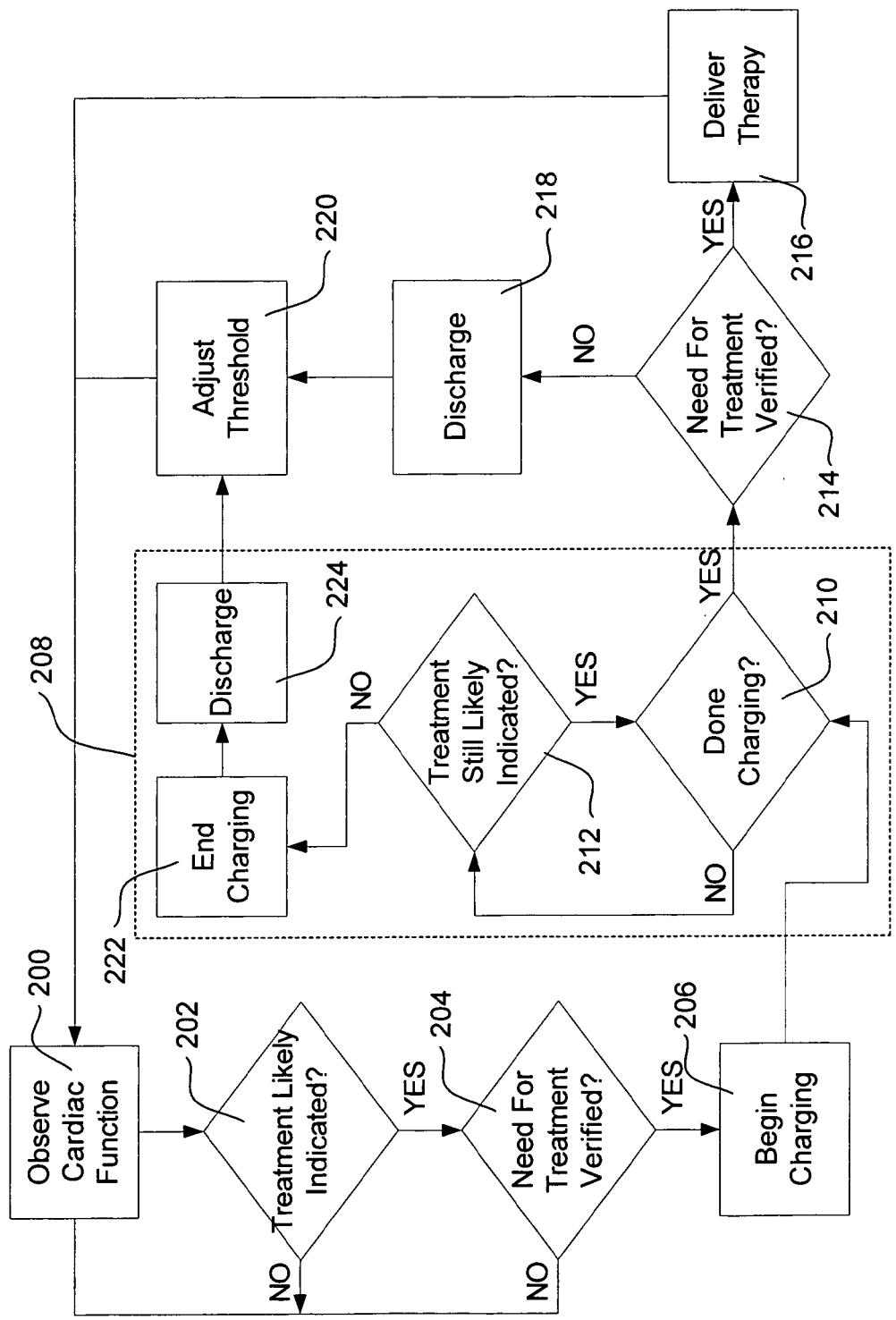
FIG. 7 illustrates a dual testing approach for charging and therapy delivery decisions.

FIG. 7 illustrates a dual testing approach for charging and therapy delivery decisions. The method begins by observing the patient's cardiac function, as shown at 200. The method then determines, as shown at 202, whether treatment is likely indicated. If treatment is not indicated, the method returns to observing cardiac function as shown at 200, where the method waits until a next cardiac event is sensed for evaluation.

If treatment is likely indicated at 202, the method next verifies that treatment is needed, as shown at 204, using a different metric than that used in step 202. One method of separating out these two steps is to observe event intervals to determine whether treatment is likely indicated (step 202) and, if so, to perform further analysis (possibly combining noise and average interval analysis) to verify that the event intervals do indeed indicate malignancy. Other first and second steps (202, 204) may be performed without deviating from the scope of the invention.

Yet another example of a first and second tier for analysis is a system wherein multiple vector views are available, for example as shown in U.S. patent application Ser. No. 10/901,258, filed Jul. 27, 2004, now U.S. Pat. No. 7,392,085 and titled MULTIPLE ELECTRODE VECTORS FOR IMPLANTABLE CARDIAC TREATMENT DEVICES, the disclosure of which is incorporated herein by reference. For example, a first sensing vector may be used for the first determination that treatment is likely indicated at 202. Additionally, a second, different sensing vector may then be used to verify that treatment is indicated at 204.

If treatment is likely indicated at 202 and a need for treatment is verified at 204, the method next includes the step of initiating the charging operation of the associated energy storage device or system (often a capacitor or group of capacitors), as shown at 206. The method next goes to a charge instruction block 208 which includes steps that are performed if the device/system is able to perform sensing and analysis operations during charging of the system's energy storage device. If sensing and analysis operations cannot be performed during charging, the method goes directly to step 214, which is explained below.

In the charge instruction block 208, the method determines whether the energy storage system is completed charging, as shown at 210. If not, the method includes observing whether treatment is still likely indicated, as shown at 212. The metric for determining whether treatment is still likely indicated in step 212 may be that of either of steps 202 or 204, or may be a yet a different metric. If treatment is still likely indicated, the method continues charging at 210 and iterates this loop until charging is complete. Once charging is complete, the method determines whether a need for treatment can be verified again, as shown at step 214. As with step 212, a metric previously used in one of steps 202, 204, or 212 may be used in step 214, or a new metric may be chosen. If the last verification step 214 is successful, then therapy is delivered as shown at 216.

If verification step 214 fails, then the stored energy may be non-therapeutically discharged, as shown at 218, in any suitable manner. Alternatively, if desired, the capacitors may continue to hold charge for a predetermined time period to assure that re-charging is not needed. One suitable manner for discharge is to use the stored energy to perform diagnostic or maintenance type functions for the device or, if the device is used for pacing, to use the energy to provide pacing energy.

Next, a threshold is adjusted, as shown at 220. Several thresholds may be adjusted, but preferably adjustment is performed on a threshold used in at least one of the preliminary steps 202, 204 that are used to make a determination that charging should be initiated at step 206. The threshold may be made more rigorous such that a decision to initiate charging at 206 becomes more difficult. The method then returns to observing cardiac function as shown at 200.

Returning to step 212, in the charge instruction block 208, if treatment is no longer likely indicated at step 212, the method terminates charging, as shown at 222, and discharges the energy storage in any suitable manner, as shown at 224. The method then goes to step 220 and adjusts a threshold as before.

As used herein, the term metric may indicate any suitable measurement or result from an analytical procedure. Example metrics include event rates, X out of Y counter ratios, and correlation results. Further metrics include a time period in which a condition (such as a cardiac tachyarrhythmia) persists or a how often an X out of Y counter is flagged.

A threshold may be rendered more rigorous in response to an aborted charge initiation. Thus, at least ostensibly, subsequent tachyarrhythmic events must be more sustainable to cross an adjusted threshold for initiating the device's charging cycle. Examples of adjustable thresholds include metrics such as event rate, X out of Y counter ratios, number of time intervals during which a malignant condition is detected, and the number of X out of Y counter flags set.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the claims are expressed.

What is claimed is:

1. An implantable cardiac stimulus device (ICSD) configured for implantation into a patient's body comprising, a housing having at least one electrode and configured to receive a lead having a plurality of electrodes, operational circuitry contained in the housing and configured to receive signals from electrodes on the lead and/or housing when the lead is received by the housing wherein the operational circuitry is configured to perform a method of cardiac signal analysis comprising:
   sensing signals from the electrodes;
   identifying detected events in the sensed signals with the intent that detected events represent cardiac events;
   determining whether a high-rate arrhythmia appears likely;
   calculating an X/Y counter in which X represents the number of detected events identified as likely indicating a malignant cardiac rhythm out of a set of Y detected events; and
   determining whether the X/Y counter indicates therapy for the patient;
   wherein the operational circuitry is configured to allow at least first and second settings for the X/Y counter, in which the second setting uses values for X and Y that are greater than values for X and Y used in the first setting and greater than 18 for X and greater than 24 for Y;
   wherein the operational circuitry is configured to identify nonsustained tachycardia in which the first setting of the X/Y counter is net and, in response to identification of nonsustained tachycardia, to adopt the use of the second setting for the X/Y counter in analyzing future cardiac rhythms to avoid unnecessary therapy delivery.

2. The ICSD of claim 1 wherein the first setting for the X/Y counter uses X=18 and Y=24.

3. The ICSD of claim 1 wherein the operational circuitry is further configured to perform the following:
   in response to determining that the X/Y counter does indicate therapy for the patient, determining whether a persistence factor is also met by determining whether the X/Y counter is met at least N times, wherein N is a predetermined quantity of at least 2.

4. The ICSD of claim 3 wherein N is configurable to have values of at least 2 and 5, wherein N is set equal to 2 by default and is increased to 5 in response to an identified nonsustained tachycardia.

5. The ICSD of claim 1 wherein the housing and lead are both configured for subcutaneous-only placement in the patient.

6. The ICSD of claim 1 wherein the housing and lead are configured for implantation in a patient as a transvenous ICD system.

7. An implantable cardiac stimulus device (ICSD) configured for implantation into a patient's body comprising, a housing having one or more electrodes and configured to receive a lead having a plurality of electrodes, operational circuitry contained in the housing configured to receive signals from the electrodes on the lead and/or housing when the lead is received by the housing, wherein the operational circuitry is configured to perform a method of cardiac signal analysis comprising:
   sensing signals from the electrodes;
   identifying detected events in the sensed signals with the intent that detected events represent cardiac events;
   determining whether a high-rate arrhythmia appears likely;
   calculating an X/Y counter in which X represents the number of detected events identified as likely indicating a malignant cardiac rhythm out of a set of Y detected events, wherein the operational circuitry is configured to allow at least first and second settings for the X/Y counter, wherein the second setting uses values for X and Y that are greater than values for X and Y used in the first setting including a value greater than 18 for X and a value greater than 24 for Y;
   determining that the X/Y counter indicates therapy for the patient and, if so, initiating a capacitor charging operation to prepare for therapy delivery; and
   after the capacitor charging operation has been initiated but before therapy delivery, determining that a malignant cardiac rhythm is not occurring and, in response, ceasing charging and allowing capacitor charge to bleed and configuring the X/Y counter to use the second setting and not the first setting.

8. The ICSD of claim 7 wherein the first setting for the X/Y counter uses X=18 and Y=24.

9. The ICSD of claim 7 wherein the operational circuitry is further configured to perform the following:
   in response to determining that the X/Y counter does indicate therapy for the patient, determining whether a persistence factor is also met by determining whether the X/Y counter is met at least N times, wherein N is a predetermined quantity of at least 2.

10. The ICSD of claim 9 wherein N is configurable to have values of at least 2 and 5, wherein N is set equal to 2 by default and is increased to 5 in response to an identified nonsustained tachycardia.

11. The ICSD of claim 7 wherein t housing and lead are both configured for subcutaneous-only placement in the patient.

12. The ICSD of claim 7 wherein the housing and lead are configured for implantation in a patient as a transvenous ICD system.

13. A method of operation in an implantable cardiac stimulus device (ICSD) configured for implantation into a patient's body comprising a housing having one or more electrodes and configured to receive a lead having a plurality of electrodes, operational circuitry contained in the housing and configured to receive signals from the electrodes on the housing and/or lead when the lead is attached to the housing, the method comprising:
   sensing signals from the electrodes;
   identifying detected events in the sensed signals with the intent that detected events represent cardiac events;
   determining whether a high-rate arrhythmia appears likely;
   calculating an X/Y counter in which X represents the number of detected events identified as likely indicating a malignant cardiac rhythm out of a set of Y detected events, wherein the operational circuitry is configured to allow at least first and second settings for the X/Y counter, wherein the second setting uses values for X and Y that are greater than values for X and Y used in the first setting including a value greater than 18 for X and a value greater than 24 for Y;
   determining that the X/Y counter indicates therapy for the patient and, if so, initiating a capacitor charging operation to prepare for therapy delivery; and
   after the capacitor charging operation has been initiated but before therapy delivery, determining that a malignant cardiac rhythm is not occurring and, in response, ceasing charging and allowing capacitor charge to bleed and configuring the X/Y counter to use the second setting and not the first setting.

14. The method of claim 13 wherein the first setting for the X/Y counter uses X=18 and Y=24.

15. The method of claim 13, further comprising, in response to determining that the X/Y counter indicates therapy for the patient, determining whether a persistence factor is also met by determining whether the X/Y counter is met at least N times, wherein N is a predetermined quantity of at least 2.

16. The method of claim 15 wherein N is configurable to have values of at least 2 and 5, wherein N is set equal to 2 by default and is increased to 5 in response to an identified nonsustained tachycardia.

17. The method of claim 13 wherein the housing and lead are both configured for subcutaneous-only placement in the patient.

18. The method of claim 13 wherein the housing and lead are configured for implantation in a patient as a transvenous ICD system.

19. An implantable cardiac stimulus device configured for implantation into a patient's body comprising a housing configured for implantation and configured to receive a lead having one or more electrodes, operational circuitry contained in the housing and configured to couple to the electrodes of the lead when the lead is received by the housing wherein the operational circuitry is configured to:
   receive cardiac signals from the electrodes;
   detect events in the cardiac signals;
   establish an X out of Y calculation from the received cardiac signals, in which X represents a quantity of detected events from the received cardiac signals which appear to indicate a need for therapy to address a malignant condition;
   monitor the X out of Y calculation by comparison to a predetermined threshold and, if the X out of Y calculation exceeds the predetermined threshold, to declare a treatable arrhythmia is occurring; and
   upon declaration of a treatable arrhythmia, prepare for therapy delivery and analyze data to determine whether a nonsustained tachycardia can be identified and if so, the operational circuitry is configured to prevent therapy from being delivered to the identified nonsustained tachycardia;

wherein the operational circuitry is further configured to set the predetermined threshold such that X=18 and Y=24 and to increase both X and Y to reduce the likelihood of subsequent declarations of treatable arrhythmia in response to nonsustained tachycardias occurring with X=18 and Y=24.

20. A method of operation for an implantable cardiac stimulus device (ICSD) configured for implantation into a patient's body, the ICSD comprising a housing configured for implantation and configured to receive a lead having a plurality of electrodes, operational circuitry contained in the housing and configured to sense signals from electrodes on the lead when the lead is received by the housing, wherein the method comprises:

the ICSD setting an initial X/Y threshold;
the ICSD sensing signals from the electrodes;
the ICSD detecting events in the sensed signals;
the ICSD establishing an X out of Y calculation from the received signals, in which X represents a quantity of detected events from the received signals which appear to indicate a need for therapy to address a malignant condition;
the ICSD monitoring the X out of Y calculation by comparison to the X/Y threshold;
the ICSD determining that the X out of Y calculation exceeds the X/Y threshold and declaring that a treatable arrhythmia is occurring;
upon declaration of a treatable arrhythmia, the ICSD preparing for therapy delivery and analyzing data to determine whether a nonsustained condition can be identified;
the ICSD determining that a nonsustained condition is occurring and withholding therapy from the patient; and
the ICSD, in response to nonsustained tachycardia, increasing both X and Y to set the X/Y threshold to reduce a future likelihood of declaration of treatable arrhythmia in the presence of a nonsustained condition by increasing X to a value greater than 18 and Y to a value greater than 24.

21. The method of claim 20 wherein at least one of the electrodes is on the housing.

22. The method of claim 20 wherein the ICSD includes a lead coupled to the housing with at least one electrode on the lead, further wherein the lead is configured for transvenous implantation, making the ICSD a transvenous system.

23. The method of claim 20 wherein the ICSD includes a lead coupled to the housing with at least one electrode on the lead, further wherein the lead is configured for subcutaneous implantation, making the ICSD a subcutaneous-only device.

* * * * *